United States Patent [19]
Goble et al.

[11] Patent Number: 5,891,134
[45] Date of Patent: Apr. 6, 1999

[54] SYSTEM AND METHOD FOR APPLYING THERMAL ENERGY TO TISSUE

[76] Inventors: Colin Goble, S. Osbourne House Clive Crescent, Penarin, S. Glanorgan, United Kingdom, CF641AT; Robert Warner, 11014 Northseal Sq., Cupertino, Calif. 95014

[21] Appl. No.: 719,133

[22] Filed: Sep. 24, 1996

[51] Int. Cl.⁶ ........................................... A61N 5/00
[52] U.S. Cl. ................. 606/27; 606/31; 606/41; 606/191; 607/101; 607/102; 607/105
[58] Field of Search ................. 606/27–31, 41, 606/42, 45–50, 191–194; 607/100–102, 104, 105, 154, 156; 604/96–103

[56] References Cited

U.S. PATENT DOCUMENTS

| | | | |
|---|---|---|---|
| 5,019,075 | 5/1991 | Spears et al. | 606/28 |
| 5,061,267 | 10/1991 | Zeiher | 606/49 |
| 5,191,883 | 3/1993 | Lennox et al. | 606/27 |
| 5,277,201 | 1/1994 | Stern | 606/41 |
| 5,344,441 | 9/1994 | Gronauer | 607/156 |
| 5,431,648 | 7/1995 | Lev | 606/27 |
| 5,460,628 | 10/1995 | Neuwirth et al. | 606/28 |
| 5,505,730 | 4/1996 | Edwards | 606/41 |
| 5,562,720 | 10/1996 | Stern et al. | 607/98 |
| 5,575,788 | 11/1996 | Baker et al. | 606/41 |
| 5,578,008 | 11/1996 | Hara | 606/27 |

FOREIGN PATENT DOCUMENTS

| | | | |
|---|---|---|---|
| 9212681 | 8/1992 | WIPO | 606/28 |

*Primary Examiner*—Michael Peffley
*Attorney, Agent, or Firm*—Emil Richard Skula

[57] ABSTRACT

An apparatus, system, and method for treating body tissue using controlled application of heat includes a control unit providing electrical power to a bipolar electrode positioned within an expandable member filled with conductive fluid. Electrical power applied to the bipolar electrode by the control unit causes current to pass from the active electrode, into the conductive fluid, and to the return electrode, thereby heating the conductive fluid. The temperature of the conductive fluid is monitored by the control unit, and power is increased and decreased in accordance with a comparison of the monitored temperature against the desired temperature range. The control unit also includes a pressure sensor for regulating the pressure in the bladder. Pressure and temperature displays and other operator controls are located on the control unit.

16 Claims, 11 Drawing Sheets

SYSTEM AND METHOD FOR APPLYING THERMAL ENERGY TO TISSUE

BACKGROUND OF THE INVENTION

1. Field of the Invention

The invention relates to a device for heating fluid in a cavity to thermally treat body tissue. More particularly, the present invention relates to an expandable device filled with a conductive fluid and having a bipolar electrode assembly to heat the conductive fluid.

2. Description of Related Art

Application of thermal energy has been used for some time to treat body tissue. One method of controlled application of thermal energy involves the use of a balloon or similar bladder filled with heated fluid. The bladder is placed against the tissue to be treated, and the heat from the fluid passes through the walls of the bladder and into the tissue.

Application of thermal energy with fluid-filled balloons has been of particular use in treating tissue in body cavities of animals, including humans. For example, balloons filled with heated fluid have been used to effect cauterization of a uterine endometrium.

A method is known for effecting necrosis of the endometrium by inserting a distensible bladder into the uterus. The distensible bladder is inflated to a predetermined pressure with a fluid so that the distensible bladder is in contact with substantially all of the tissue lining for which necrosis is desired. The fluid is heated to a temperature sufficient to ablate the tissue lining. The temperature and pressure of the fluid is controlled by means connected to the distensible bladder. The bladder is maintained inflated with the fluid at a temperature for a period of time sufficient to effect necrosis of the endometrium.

Early methods for heated-balloon therapy required the fluid to be preheated outside the body, and then pumped through conduits into the balloon or other bladder. However, such methods may cause heat to build up around the conduits as they pass into the body cavity, which may cause unwanted heating of body tissue adjacent to the entry into the body cavity. Another previous method for heated-balloon therapy involved positioning a heating element coil in the balloon, and causing an electrical current to pass through the coil, thereby heating the coil and the surrounding fluid.

Consequently, there is a need to improve heated fluid systems to provide rapid and uniform heating while at the same time allowing a user to monitor and control the fluid temperature. The present invention satisfies these needs.

SUMMARY OF THE INVENTION

Briefly and in general terms, the present invention provides an apparatus, system, and method for heating fluid in a cavity. More particularly, the present invention is a device and method for inducing an electrical current in a conductive fluid in a cavity, and thereby heating the conductive fluid.

Briefly and in general terms, the present invention provides an apparatus, system, and method for applying heat to body tissue, such as for endometrial ablation. The apparatus provides for heating of an inflation medium within a distensible bladder positioned adjacent to the tissue to be treated. The invention has particular application in providing a safe and efficacious method for ablating the endometrium of the uterus. The present invention thus provides a relatively inexpensive and easy method to treat menorrhagia in women.

In one embodiment, the invention includes an apparatus for treating tissue at a selected operation site, including a distensible bladder with an electrode assembly positioned therein, which is preferably a bipolar electrode assembly including one or more active electrodes and one or more return electrodes. The bladder is filled with a conductive fluid such as a saline solution. The apparatus may include a shield that prevents one or both electrodes from contacting the bladder. The shield may be a part of one of the electrodes.

The apparatus may be part of a system including a control unit providing electrical energy, such as RF energy, to the electrode. The control unit may monitor the fluid temperature, either through the use of temperature sensors or by monitoring the impedance across the bipolar electrodes, and adjust power to maintain the fluid temperature within a desired range, The control unit may have a display for showing fluid temperature and/or pressure, and may include an alarm for indicating an undesired level of fluid temperature and/or pressure. The control unit may also include a multiplexer for independently controlling the delivery of power to individual electrodes in the electrode assembly.

In a further embodiment, the inner surface of the bladder may be conductive so that it acts as an electrode. The bladder may have a plurality of electrodes on its inner surface, with individual electrodes independently controlled by the control unit.

In a further embodiment, the apparatus uses an expandable cage instead of a distensible bladder. The expandable cage may be conductive and act as one or more electrodes of the electrode assembly.

In another embodiment, the invention is a method of treating tissue using a surgical device, including an expandable device and a bipolar electrode assembly with at least one active electrode and at least one return electrode, including the steps of: introducing the distal end of the surgical device into a selected operation site; expanding the expandable device; filling the expandable device with a conductive saline solution; and applying output power to the bipolar electrode assembly to heat the conductive fluid. The method may include the further steps of monitoring the fluid temperature, and controlling the output power to the electrode assembly to maintain the temperature of the conductive fluid in a desired temperature range. The temperature may be determined by monitoring the impedance between the active electrode and return electrode.

In a further embodiment, the electrode assembly is used not only to heat the conductive fluid but also to treat specifically targeted tissue. In such a method, the electrode assembly is preferably movable within the expandable device, and can be positioned adjacent specifically targeted tissue. Such a method is of particular use with an expandable device comprising an expandable cage.

Other features and advantages of the present invention will become more apparent from the following detailed description of the invention when taken in conjunction with the accompanying drawings.

DETAILED DESCRIPTION OF THE PREFERRED EMBODIMENTS

The present invention is depicted in FIGS. 1–11 for use in body cavities, including use in ablating the endometrial lining of a patient's uterus. However, the present invention is not limited to use in the uterus, and may be applied to techniques for thermal treatment of a variety of tissue, including the treatment of tissue within a variety of body cavities such as the bladder, the gall bladder, portions of the gastrointestinal tract, the heart, and other body cavities. The invention may be used in a variety of procedures, including thermal treatment of hemorrhoids, intestinal walls, the lining of the rectum, the lining of the bladder, etc. Moreover, the invention may also be used for heating fluid in a variety of applications where controlled application of heat is desired, and not just for the treatment of tissue.

Figure 1:
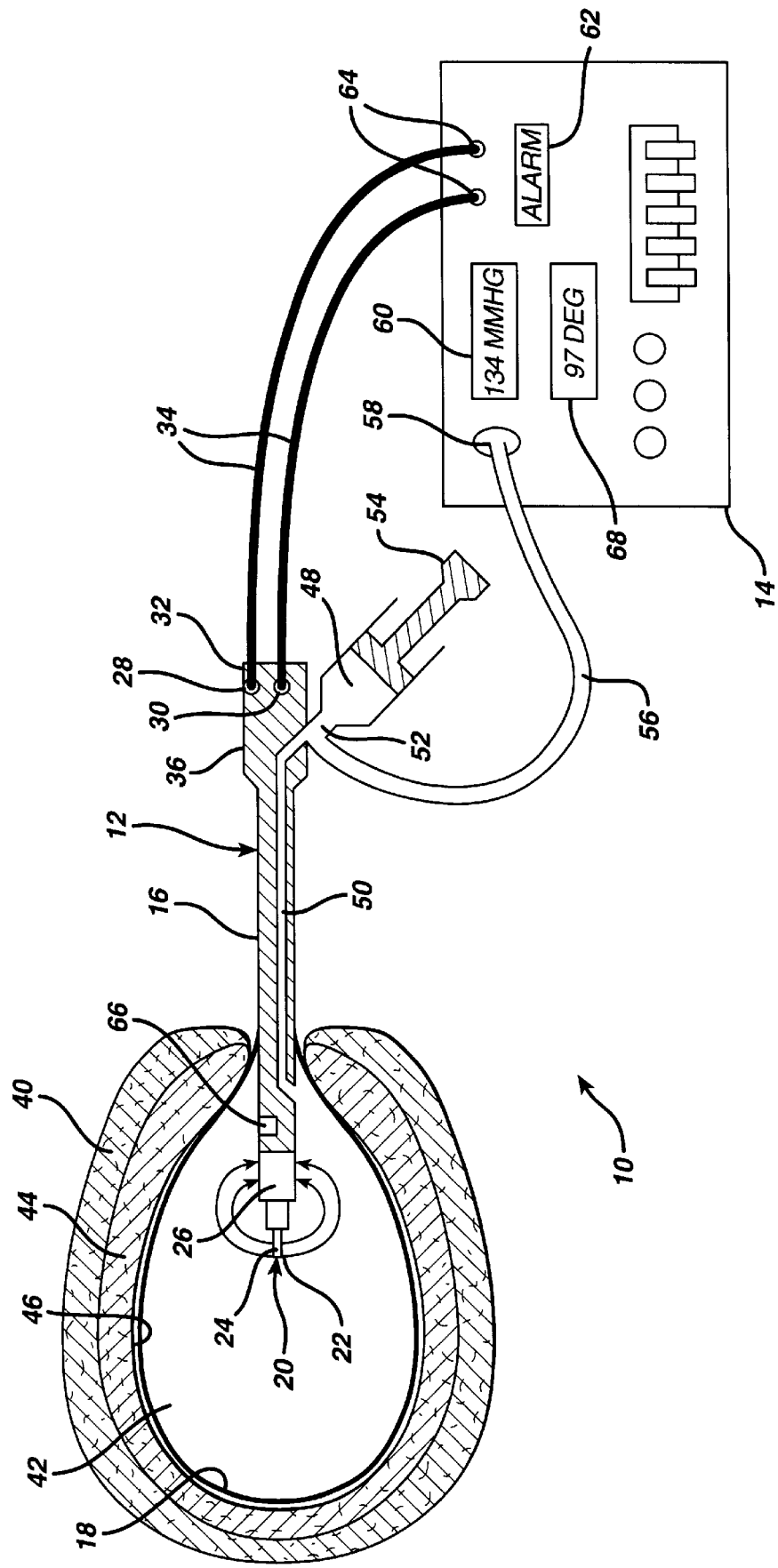
FIG. 1 depicts, in partial section, a system according to the present invention, including a control unit and treatment catheter having a distensible bladder, with the distensible bladder inserted into and inflated within the uterus of a patient.

Referring now to FIG. 1, in one preferred embodiment the system 10 of the invention comprises a catheter 12 and a control unit 14. The catheter 12 includes a generally elongated shaft 16 having a distensible bladder 18 and electrode assembly 20 at its distal end 22. The electrode assembly 20 is positioned in and surrounded by the distensible bladder 18. The electrode assembly 20 comprises an active electrode 24 and a return electrode 26, and may be of the type shown and described in pending U.S. patent application Ser. No. 08/702,512 entitled "An Electrosurgical Instrument," which is incorporated herein by reference. Alternatively, the electrode assembly 20 of the current invention may have greater spacing between the active electrode 24 and return electrode 26, thereby increasing the minimum distance for current to must pass between the active electrode 24 and return electrode 26. Thus, thermal distribution may be improved.

In the embodiment of FIG. 1, the active electrode 24 and return electrode 26 are in electrical contact with electrical connectors 28, 30 that are in turn in electrical contact with the control unit 14. In the embodiment of FIG. 1, the electrical connectors 28, 30 are located at the proximal end 32 of the catheter shaft 16, and are removably secured to the control unit 14 via cables 34. The catheter shaft proximal end 32 has a handle 36 by which a user may grasp the device.

FIG. 1 shows the distal end 22 of the instrument shaft 16 placed in a body cavity, which in the embodiment shown is a human uterus 40. The bladder 18 is inflated with a conductive fluid 42, such as a saline solution, to a pressure sufficient to ensure firm contact with the endometrial tissue layer 44 on the interior uterine surface 46.

Electrical power is provided to the electrode assembly 20 to cause current to flow between the active electrode 24 and return electrode 26 and through the conductive fluid 42, thereby heating the conductive fluid 42. The method provides for heating the conductive fluid 42 within the distensible bladder 18 to a desired temperature, and maintaining the temperature and pressure within the distensible bladder 18 for a desired time interval. Afterwards, the distensible bladder 18 is deflated and the catheter shaft 16, including the distensible bladder 18 and electrode assembly 20, is removed from the patient's uterus 40.

The bladder 18 must be capable of withstanding high temperatures without rupturing, and preferably have good heat transfer characteristics to provide efficient heating action. A distensible bladder of a heat-curing rubber, such as latex rubber, has been found satisfactory in similar applications. The bladder may be formed of elastic or inelastic materials.

Inflation of the bladder 18 may be accomplished through various ways. In the embodiment of FIG. 1, conductive fluid 42 is introduced into the bladder 18 using a fluid source, such as a syringe 48, in fluid contact with the bladder 18 via a fluid line 50 and fluid fill port 52 that leads to the bladder 18. Manipulation of the syringe 48, by depressing a plunger 54, causes conductive fluid 42 to be introduced into the distensible bladder 18, forcing the distensible bladder 18 to expand into contact with the endometrial tissue layer 44 of the uterus 40. The conductive fluid 42 is also directed along flexible tubing 56 to the control unit 14, where the pressure is measured by a sensor such as a pressure transducer 58. All parts of the fluid path, including the bladder 18, fluid line 50, and flexible tubing 56, are in fluid communication, thus providing constant fluid pressure within the entire fluid system and allowing measurement of bladder pressure by monitoring the pressure within the flexible tubing 56. The control unit 14 monitors the fluid pressure and shows the pressure on a pressure display monitor 60.

In many procedures, it is desirable to monitor and maintain the fluid pressure within a desired range, with the desired pressure range depending on the particular application. The pressure display monitor 60 located on the control unit 14 shows the pressure to the user. If the pressure in the distensible bladder 18 is beyond a desired range, a warning signal and/or alarm 62 alerts the user that the pressure is either too low or too high. To adjust the pressure, the user may manually manipulate the plunger 54 of the syringe element 48. Alternatively, the control unit 14 may include a pump or similar device (not shown) in fluid contact with the bladder 18 that automatically provides or removes conductive fluid 42 from the bladder 18 to regulate the pressure to maintain the pressure within a selected range.

The control unit 14 provides power to the electrode assembly 20 via the electrical ports 64, to which are secured the connecting cables 34 that link the connectors 28, 30 of the active and return electrodes 24, 26. The power provided may be of a variety of types and power levels. AC and/or DC power may be used, depending on the particular use and circumstances. Radio-frequency (RF) power has particular application with the invention, as does pulse-width modulation.

The current flow between active and return electrodes 24, 26 heats the conductive fluid 42. The temperature of the fluid 42 is monitored by the control unit 14, either via a temperature sensor 66 positioned in the bladder 18, an impedance vs. temperature calculation, or other means. The temperature is preferably shown on a temperature display 68 on the control unit. In a preferred embodiment, the control unit 14 compares the monitored temperature to the desired temperature and automatically adjusts the power to compensate for temperature changes. If the monitored temperature is above a desired range, power is reduced to allow the fluid to cool. If the monitored temperature is below a desired range, power is increased to heat the fluid. If temperature is beyond a selected range, the control unit may activate the alarm 62.

The control unit 14 may comprise a generator of the type described in pending U.S. application Ser. No. 08/642,121, filed May 2, 1996, entitled "An Electrosurgical Generator And System," which is incorporated herein by reference. In a preferred embodiment, the control unit 14 includes a generator having a radio frequency (RF) power oscillator with an electrical connection, such as a pair of output connection ports 64, for coupling, via one or more cables 34, to the catheter 12 and electrode assembly 20. When RF power is applied to the electrode assembly 20, the conductive fluid 42 heats up. If the conductive fluid 42 is a saline solution such as 0.9% w/v, the temperature coefficient of the fluid 42 is positive, so that the corresponding impedance coefficient is negative. As power is applied, the impedance between the active electrode 24 and return electrode 26 initially falls and continues to fall with increasing dissipation of power.

If sufficient power is applied, a vapor bubble may form about the active electrode 24. As the saline in immediate contact with the active electrode 24 reaches its boiling point, vapor bubbles may form on the surface of the active electrode 24, which necessarily cause the impedance across the electrodes 24, 26 to rise. As power is further increased, the impedance will continue to rise as the vapor bubbles enlarge to form a vapor pocket about the active electrode 24.

As the vapor pocket begins to form about the active electrode 24, there is an increase in the power density at the residual electrode/saline interface. Initially, there is an exposed area of the active electrode 24 that is not covered by the vapor bubbles. This exposed area becomes the preferred electrical path, further stressing the interface by producing more vapor bubbles and even higher power density. The formation of the vapor pocket quickly becomes a runaway condition that only reaches equilibrium once the active electrode is completely enveloped in the vapor pocket.

Once the vapor pocket completely envelopes the active electrode 24, the impedance rapidly increases to around 1000 ohms, with the actual impedance value dependent upon system variables. Power passes from the active electrode 24 to the conductive fluid 42 via electrical discharges across the vapor pocket. The majority of the power dissipation occurs within this pocket, with consequent heating of the active electrode 24. The amount of energy dissipated, and the size of the vapor pocket, depends on the output voltage. Maintaining the vapor pocket without destroying the active electrode requires a delicate balance of output voltage. If it is too low, the pocket will not be sustained. If it is too high, the electrode assembly 20 can be destroyed. Accordingly, once the impedance has reached a certain point indicating formation of the vapor pocket, the power must be reduced to a selected level.

It is generally important to control, and possibly prevent, formation of the vapor pocket about the active electrode 24 in order to maximize the efficiency of heating the conductive fluid. By increasing the distance between the active electrode 24 and return electrode 26, thermal distribution can be improved, thereby increasing the upper limit of power delivery before the onset of vaporization. For example, if sufficient power is applied, the vapor pocket might create significant amounts of steam in the bladder, which can have undesirable effects such as the creation of a large vapor buildup at the top of the bladder that can significantly reduce the thermal transfer efficiency. The boiling vapor pocket may also create undesired noise. To control the formation of the vapor pocket and the temperature of the conductive fluid, the control unit 14 monitors the peak RF voltage appearing across the output connection ports 64 of the control unit 14, which corresponds to the voltage across the active electrode 24 and return electrode 26, and rapidly reduces the delivered output power whenever a selected peak voltage threshold is reached. Accordingly, the control unit 14 can monitor the impedance and control output power to prevent the formation of vapor bubbles. This may be achieved by detecting an impedance increase that indicates the initial formation of vapor bubbles, and rapidly reducing power to prevent formation of a vapor pocket. Alternatively, the control unit 14 can monitor the impedance and control output power to form and maintain a vapor pocket.

Figure 2:
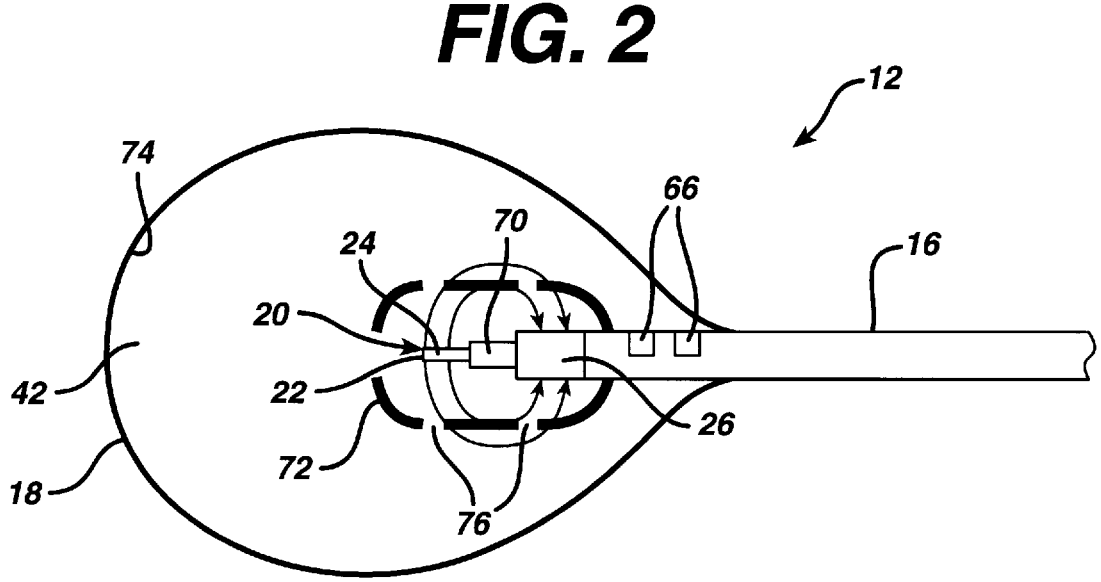
FIG. 2 is a side view, in partial section, of a heated bladder device according to a preferred embodiment of the invention.

In the preferred embodiment shown in FIG. 2, the electrode assembly 20 is a bipolar electrode having an active electrode 24 and a return electrode 26. However, the system would still operate if the polarity were reversed, i.e., if the active electrode 24 served as a return electrode, with the return electrode serving as an active electrode. Additionally, where AC power is used with the system, the terms "active electrode" and "return electrode" lose their traditional "negative/positive" meanings. For AC applications, the terms "active" and "return" are used to refer to the electrodes having opposing polarities. Where the electrodes have differing sizes in AC applications, the term "active electrode" is generally used to refer to the smaller electrode, and the term "return electrode" is generally used to refer to the larger electrode.

The active electrode 24 of FIG. 2 is positioned at the extreme distal tip of the catheter shaft 16. The return electrode 26 is proximal of and coaxial with the active electrode 24. In the particular embodiment shown in FIG. 2, the effective area of the return electrode 26 is substantially greater than the effective area of the active electrode 24. However, the effective areas of the electrodes 24, 26 may vary significantly in different embodiments, depending on the particular electrode assembly. For example, in various embodiments of the invention, the active and return electrodes may have substantially equal areas, or the active electrode may be substantially larger than the return electrode.

In FIG. 2, the active and return electrodes 24, 26 are separated by an insulator 70, such as a ceramic material. As shown roughly in FIG. 2, when power is applied to the electrode assembly 20, current flows from the active electrode 24, through the conductive fluid 42, and into the return electrode 26. The interaction of the current with the conductive fluid 42 heats the fluid 42.

In addition to heating the fluid 42, the interaction of the current with the conductive fluid 42 can also create a magnetohydrodynamic effect that causes stirring of the fluid within the bladder 18. This fluid stirring can be relatively intense, depending on the particular electrode configuration and the type and level of electrical power provided. The fluid stirring is particularly intense when RF power or pulse-width modulation is used. The magnetohydrodynamic stirring can be beneficial in helping to maintain relatively constant fluid temperatures throughout the bladder 18.

An additional advantage of the invention is the ability to determine the temperature of the conductive fluid 42 using impedance/resistivity. Many conductive fluids have resistivities/impedances that are temperature dependent, so the temperature may be calculated from resistivity/impedance. For example, saline solution is a negative-temperature-coefficient material (i.e., it has a positive thermal coefficient of conductivity, which is a negative thermal coefficient of impedance), so that a small change in temperature causes a large corresponding change in the impedance/resistivity of the saline solution. Because the impedance/resistivity are temperature dependent, the temperature of the conductive fluid 42 in the bladder 18 can be accurately determined by monitoring the impedance/resistivity between the active and return electrodes 24, 26.

An advantage of using the impedance/resistivity between the electrodes 24, 26 is that the resulting temperature is based upon the path of the electrical current, which flows through all the conductive fluid 42 within the distensible bladder 18. The current path between the two electrodes 24, 26 passes, at varying levels, through the entire body of conductive fluid 42 in the bladder 18. Accordingly, rather than giving a temperature measurement of just an isolated position in the fluid, as would be the case with a conventional temperature sensor, an impedance-based temperature determination gives a more accurate measurement of overall fluid temperatures in the bladder 18.

As shown in FIG. 2, the catheter may include one or more temperature sensors 66 for monitoring temperature within the conductive fluid 42. These temperature sensors 66 may be in lieu of or in addition to the impedance-based temperature measurement. The temperature sensors may employ a variety of sensor types and techniques, including thermocouples, thermistors, RTD (resistance temperature device), curie-point method, photofluorescent decay, etc. The particular selection of temperature sensor may depend on the particular application. For example, because thermocouples can be sensitive to RF noise, another type of temperature sensor may be desirable for applications where the control unit generates RF energy for the electrode assembly.

The control unit 14 may use the impedance-based temperature measurement, the measurement from the temperature sensors 66, or a combination thereof to regulate the power delivered to the electrode assembly and/or the temperature shown on the temperature display 68. When the fluid temperature is too high, the power can be reduced. If the fluid temperature is too low, the power can be increased.

The catheter 12 may include a shield 72 that generally surrounds the electrode assembly 20. The shield 72 prevents the electrode assembly 20, and particularly the active electrode 24, from contacting and/or damaging the bladder wall 74. In the embodiment of FIG. 2, the shield 72 has a plurality of openings 76 which allow conductive fluid 42, as well as electrical current, to pass freely therethrough. In alternative embodiments, the shield 72 may comprise a cage or mesh assembly.

In the embodiment shown in FIG. 2, the shield 72 surrounds both the active electrode 24 and return electrode 26. However, depending on the particular application and power involved, the shield 72 may surround either the active electrode 24 or the return electrode 26, but not necessarily both. Due to the size difference between the active electrode 24 and return electrode 26, the active electrode 24 generally is much hotter than the return electrode 26. Thus, contact between the bladder wall 74 and the return electrode 26 may result in no damage to the bladder wall 74, while contact between the active electrode 24 and the bladder wall 74 at the same power input might cause severe damage to the bladder wall 74. Accordingly, protecting the bladder 18 from contact with the return electrode 24 may not always be necessary, even in situations where the bladder wall 74 must be protected from contact with the active electrode 24.

Figure 3:
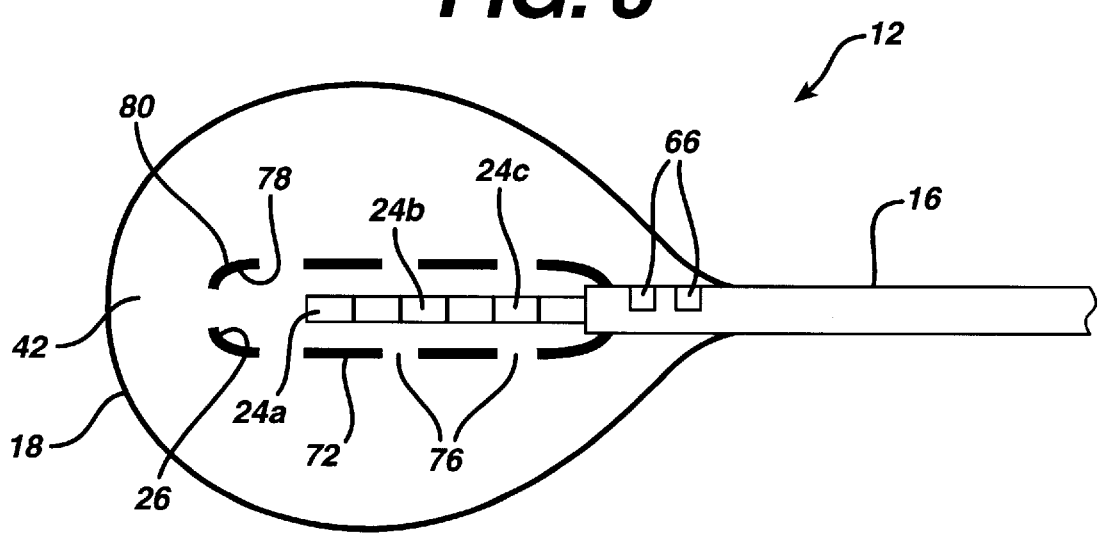
FIG. 3 is a side view, in partial section, of a heated bladder device according to a further embodiment of the invention.

In another embodiment of the invention, the shield 72 acts as the return electrode 26, as shown in FIG. 3. The inner surface 78 of the shield 72 is conductive and acts as the return electrode 26, while the shield outer surface 80 is non-conductive. However, the system would also operate if the outer surface 80 of the shield were conductive. Because the return electrode 26 is so much larger in effective area than the active electrodes 24a–c, the power is largely dissipated across the return electrode 26, i.e., across the shield 72. Accordingly, heat and energy buildup is much less than in the active electrode 24a–c and, depending on the particular electrode configuration, bladder, and power involved, the return electrode 26/shield 72 may be able to contact the bladder wall 74 during a procedure without harming the wall 74.

Note that the invention is not limited to the shield being a return electrode. For example, in the example of FIG. 3, the shield 72 could serve as an active electrode, with the (formerly active) electrodes 24a–c serving as return electrodes. Additionally, the invention is not limited to a single active electrode or a single return electrode. Almost any number of active electrodes and return electrodes may be used. Additionally, the number of active electrodes does not have to equal the number of return electrodes. For example, in the embodiment of FIG. 3, there are three active electrodes 24a, 24b, 24c, but only one return electrode 26. The active electrodes 24a, 24b, 24c may be individually controlled, so that power is applied to individual or groups of active electrodes as desired.

Figure 4:
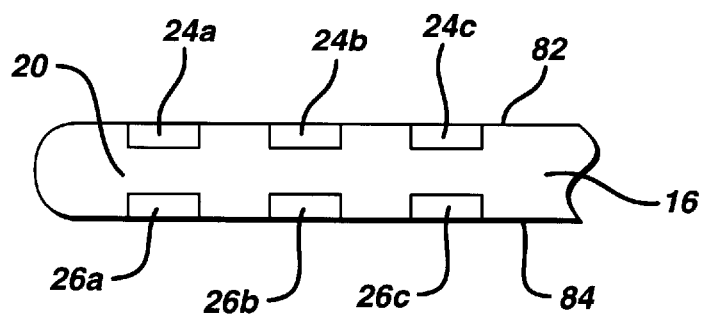
FIG. 4 is a side view of an electrode assembly according to another embodiment of the invention.

FIG. 4 shows another embodiment of a catheter 12 with multiple active electrodes 24a–c, but also having multiple return electrodes 26a–c. Three active electrodes 24a–c are located on a first side 82 of the catheter shaft 16, and three return electrodes 26a–c are located on a second side 84. The electrodes 24a–c, 26a–c are separated by an insulating material 70. In such an embodiment, all electrodes 24a–c, 26a–c may be activated simultaneously. Alternatively, the electrodes 24a–c, 26a–c may be activated in sets. For example, if the system desired the fluid in the distal portion of the bladder to have greater heat, just the most distal active electrode 24a and return electrode 26a might be activated.

Figure 5:
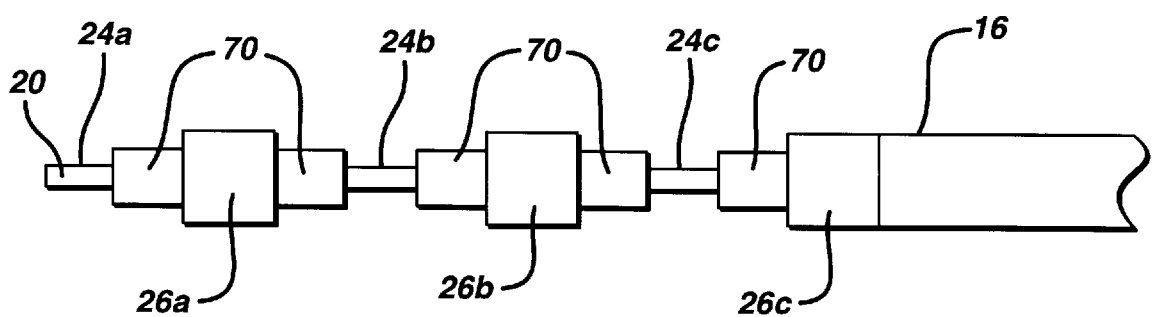
FIG. 5 is a side view of an electrode assembly according to another embodiment of the invention.

FIG. 5 shows another embodiment of a catheter 12 having multiple active electrodes 24a–c and return electrodes 26a–c, but with the electrodes 24a–c, 26a–c coaxially positioned in alternating order on the catheter shaft 16 and separated by an insulating material 70. As with the embodiment of FIG. 4, the electrodes 24a–c, 26a–c are preferably capable of independent activation, so that the application of energy can be controlled with greater accuracy.

Figure 6:
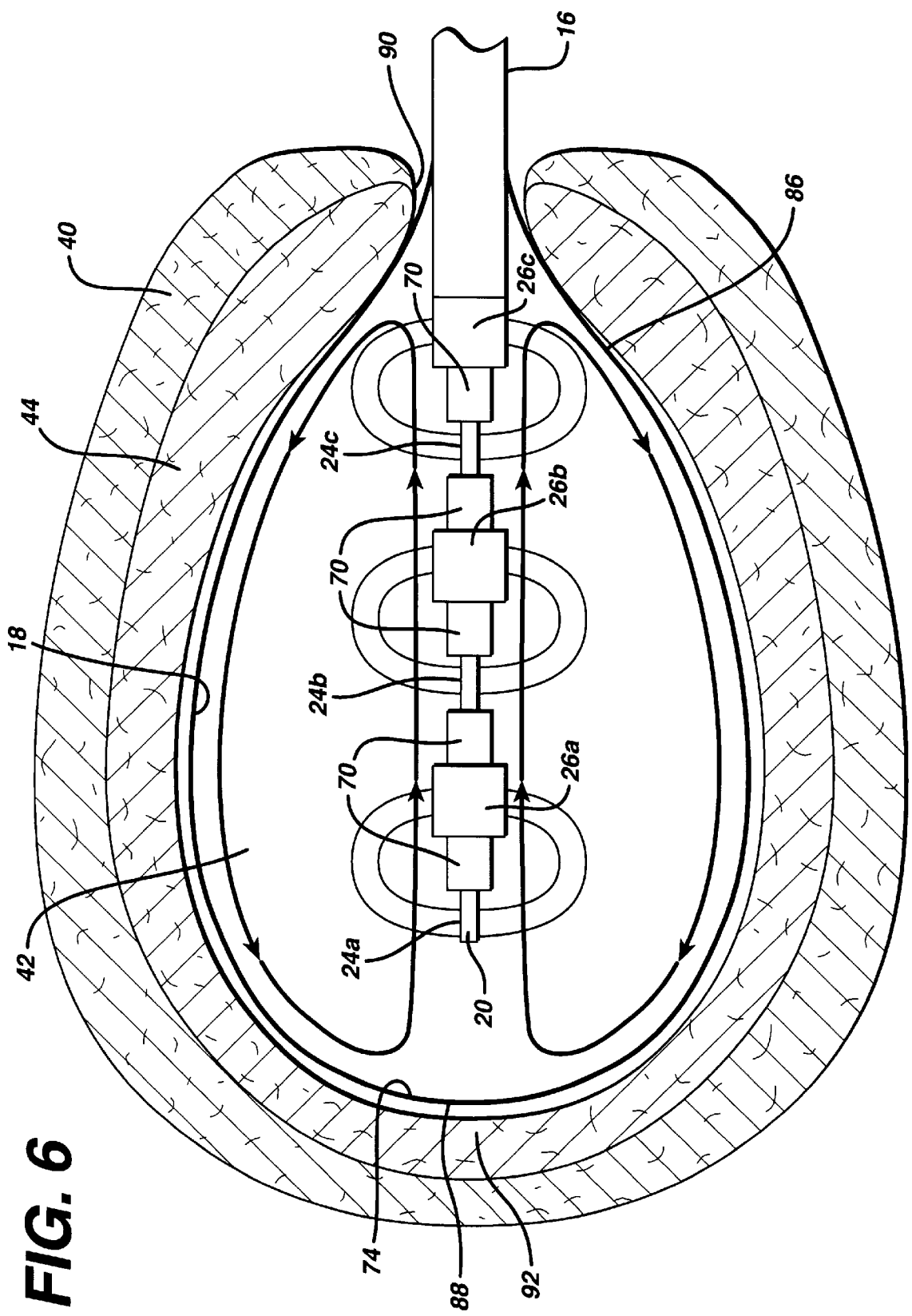
FIG. 6 is a side view, in partial section, of a heated bladder device according to a further embodiment of the invention.

Individually controlled electrodes 24a–c, 26a–c can be used in combination with a control unit having a multiplexer used to chop the power output to enhance the convective stirring effect induced by the temperature gradients within the conductive fluid. The control unit can control the output power to individual electrodes 24a–c, 26a–c to induce a selected fluid flow within the bladder 18. For example, by independently and sequentially activating matched or unmatched pairs of electrodes, a selected flow can be induced in the bladder. FIG. 6 shows sequential activation of the most distal active electrode 24a and return electrode 26a, then the middle active electrode 24b and return electrode 26b, and then the most proximal active electrode 24c and return electrode 26c, a generally circulating flow can be induced that causes the conductive fluid 42 to flow along the catheter shaft 16 in a proximal direction, then flows along the bladder wall 74 in a distal direction to complete the flow pattern shown in FIG. 6.

An advantage to controlling the fluid flow is that high-temperature fluid can be concentrated in selected areas of the bladder 18. For example, in the example shown in FIG. 6, the fluid passing proximal along the catheter shaft 16 receives the greatest heat due to its proximity to the electrodes 24a–c, 26a–c. Conversely, as the fluid passes distally along the bladder wall 74, it cools. Such a flow has the desirable effect of concentrating the hottest fluid at the bladder proximal end 86, with cooler fluid at the bladder distal end 88. In endometrial ablation procedures, greater heat is generally required to treat thicker portions of the endometrial layer 44. As shown in FIG. 6, the thickest portions of the endometrial layer are closest to the cervix 90, i.e., are adjacent to the proximal end 86 of the distensible bladder 18, where the hottest conductive fluid is directed. Conversely, the thinnest portions of the endometrial layer are at the back of the uterus 92, which is adjacent the distal portion 88 of the bladder 18 with the coolest conductive fluid.

Figure 7:
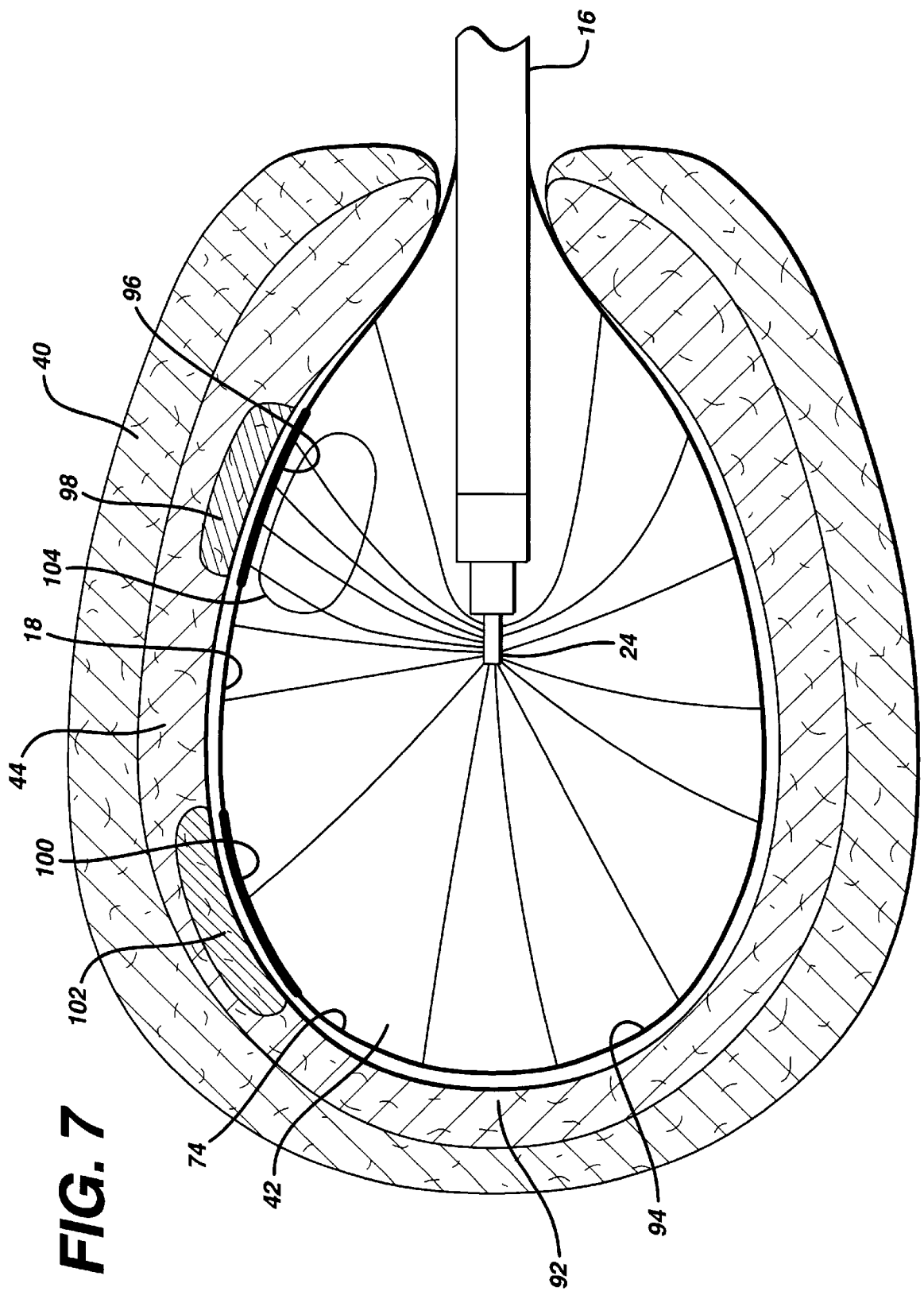
FIG. 7 is a side view, in partial section, of a heated bladder device having a conductive inner surface according to an embodiment of the invention.

FIG. 7 shows a further embodiment of the invention, wherein the inner surface 94 of the distensible bladder 18 functions as the return electrode, and the active electrode 24 is positioned at the end of the catheter shaft 16. The bladder 18 itself may be formed of a conductive material. Alternatively, the bladder may be generally non-conductive, but may have a conductive inner surface 94. For example, a conductive material may be deposited on the inside of the bladder 18 to form a conductive inner surface 94. An example would be a sputter deposition of a conductive metal such as gold or silver.

When power is applied to the device, electrical current passes between the active electrode 24 and the conductive inner surface 94, via the conductive fluid 42. The conductive fluid is heated in the process. If the conductive inner surface 94 of the bladder 18 is a positive-temperature-coefficient material (i.e., has a negative thermal coefficient of conductivity), such as gold or silver, the resistivity/impedance of the inner surface 94 increases as the temperature increases. Thus, current will necessarily be drawn more readily to a cooler area 96 of the bladder wall 74. Such behavior is particularly advantageous for ablating tissue, such as the endometrial lining 44 of the uterus 40. As tissue is ablated, it looses much of its ability to absorb heat from the adjacent bladder wall 74. Accordingly, a bladder wall portion 96 overlying non-ablated tissue 98 will be generally cooler than a bladder wall portion 100 immediately overlying ablated tissue 102. Because cooler portions of bladder wall are more conductive, greater amounts of electrical power will be directed to a cooler bladder wall portion 96, necessarily causing increased heat to be delivered to the conductive fluid adjacent to the wall, i.e., toward the non-ablated tissue 98, so that ablation of non-ablated tissue 98 is facilitated. Conversely, for ablated tissue 102, the overlying portion of bladder wall 100 heats up, thereby acquiring greater resistivity/impedance, and less electric power will be directed to the conductive fluid adjacent to site. Thus, any chance of tissue scorching will be reduced, while even tissue ablation is encouraged.

The above effect is further enhanced when a negative-temperature-coefficient conductive fluid is used, such as saline solution. As the flow of electrical current toward the cooler bladder wall portion 96 increases, the conductive fluid 104 adjacent to that cooler bladder wall portion 96 will increase in temperature, which necessarily increases the conductivity of the hotter conductive fluid 104. Thus, a relatively cool wall portion 96, with adjacent fluid 104 that is hotter than the average fluid temperature, will receive greater electrical energy than a warmer wall portion 100.

Because the bladder wall 74 is in contact with the endometrial tissue 44, it will cool more rapidly than the conductive fluid just inside the wall, especially when the underlying tissue is not ablated. Heat will readily pass from the heated liquid, through the bladder wall, and into the unablated tissue. However, as the tissue ablates, the passage of heat into the tissue will be reduced, and heat will start to build up in the bladder wall. As this occurs, the current flow to the bladder wall conductive inner wall decreases, and the fluid temperature adjacent to the area will also decrease. Accordingly, the device will maximize the efficiency of tissue ablation, delivering greater thermal energy to non-ablated tissue.

Figure 8:
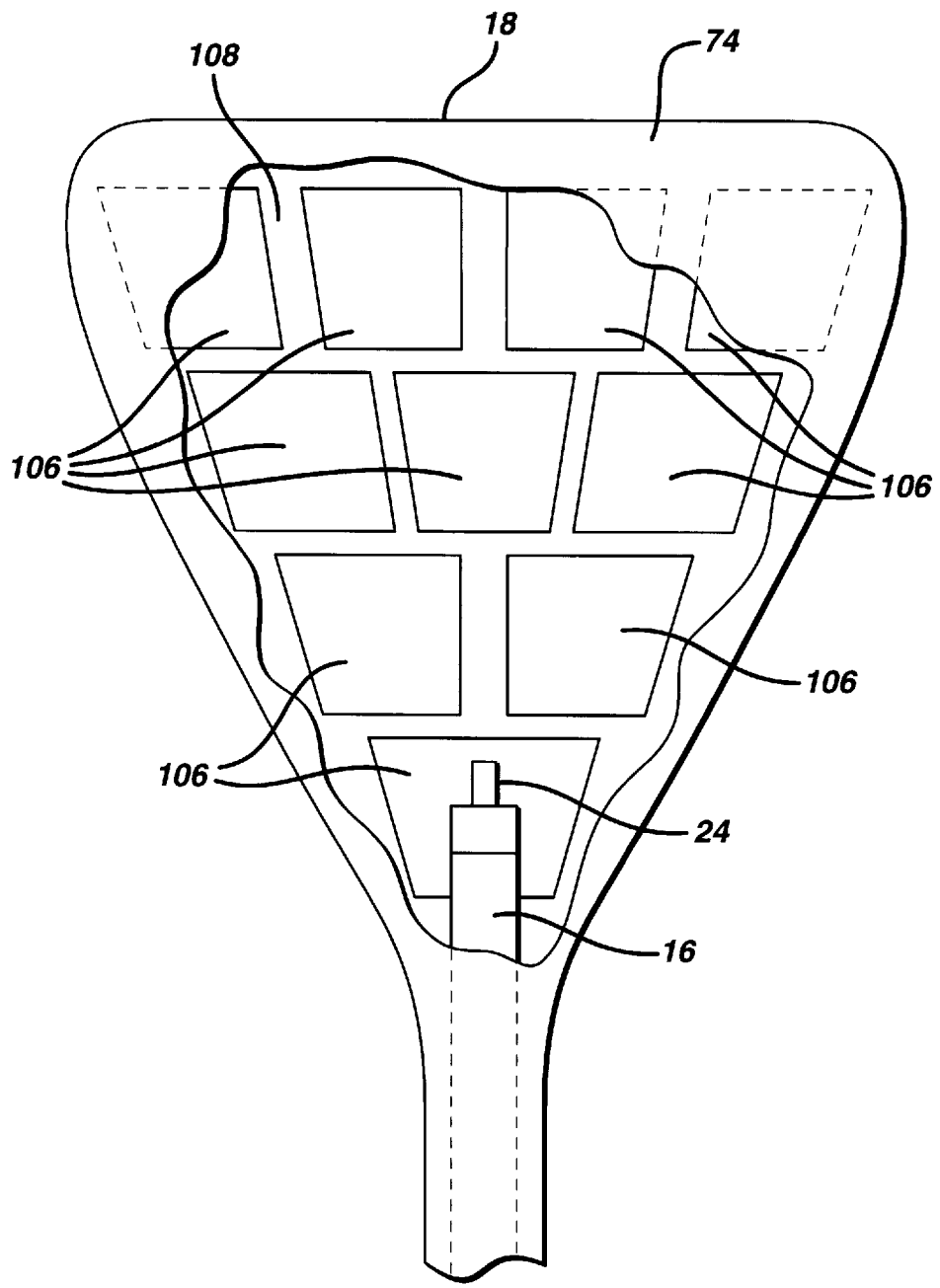
FIG. 8 is a top view, in partial section, of a heated bladder device having multiple electrodes on its inner surface according to another embodiment of the invention.

FIG. 8 shows a further embodiment of the invention, wherein a bladder 18 has a plurality of individual electrodes 106 on its inner surface 108. In the embodiment shown, the individual electrodes 106 are return electrodes, and one or more active electrodes 24 are positioned within the bladder 18. Each of the return electrodes 106 is individually controlled. For example, a particular electrode may be activated based on the temperature of that particular electrode and/or of the bladder wall immediately underlying the electrode. Once a certain temperature was reached by a section of bladder wall, the electrode thereon would be shut off, so that no further energy would be delivered to the site. Thus, the device can be used to direct greater energy to cooler portions of the bladder wall 74, without relying on the interaction of the current with temperature coefficient of a conductive bladder wall to direct the energy (as in FIG. 7). The user could also directly control the activation of the individual electrodes to direct greater and lesser energy to selected tissue areas, so that certain tissue areas might be ablated to greater depths, some tissue areas may be only slightly ablated, and some tissue areas may be completely unablated.

In the embodiment of FIG. 8, the bladder 18 is generally V-shaped to conform to an intrauterine cavity. However, a variety of bladder shapes may be used with the various embodiments of the invention, depending on the particular application. Moreover, the types of bladders and the materials used therein can vary widely. Bladders can be formed of expandable materials such as heat-cured rubber, or generally non-stretchable materials.

Figure 9A:
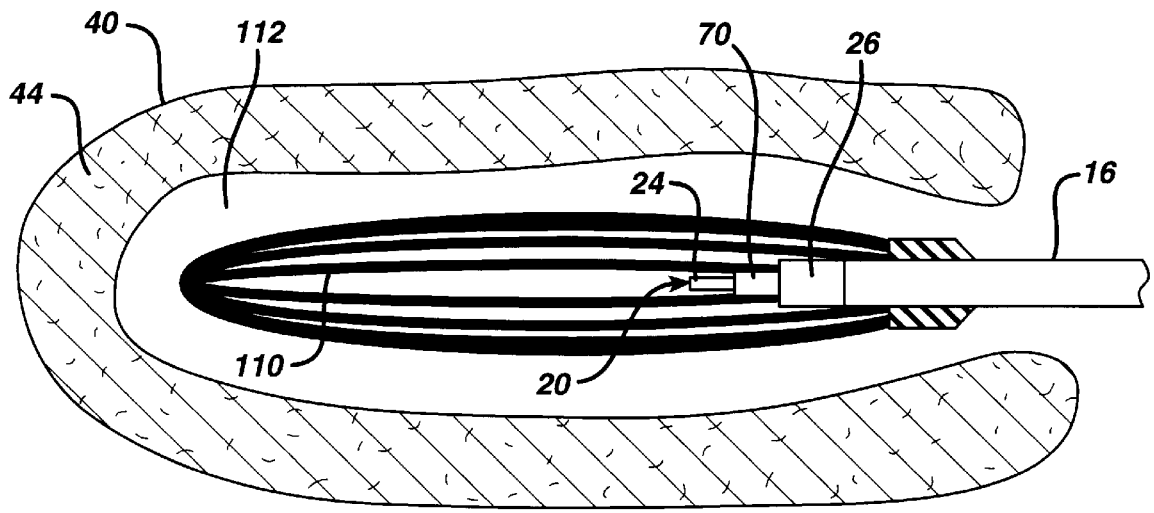
FIG. 9a is a side view, in partial section, of a heated device with an expandable cage in a collapsed, delivery configuration.
Figure 9B:
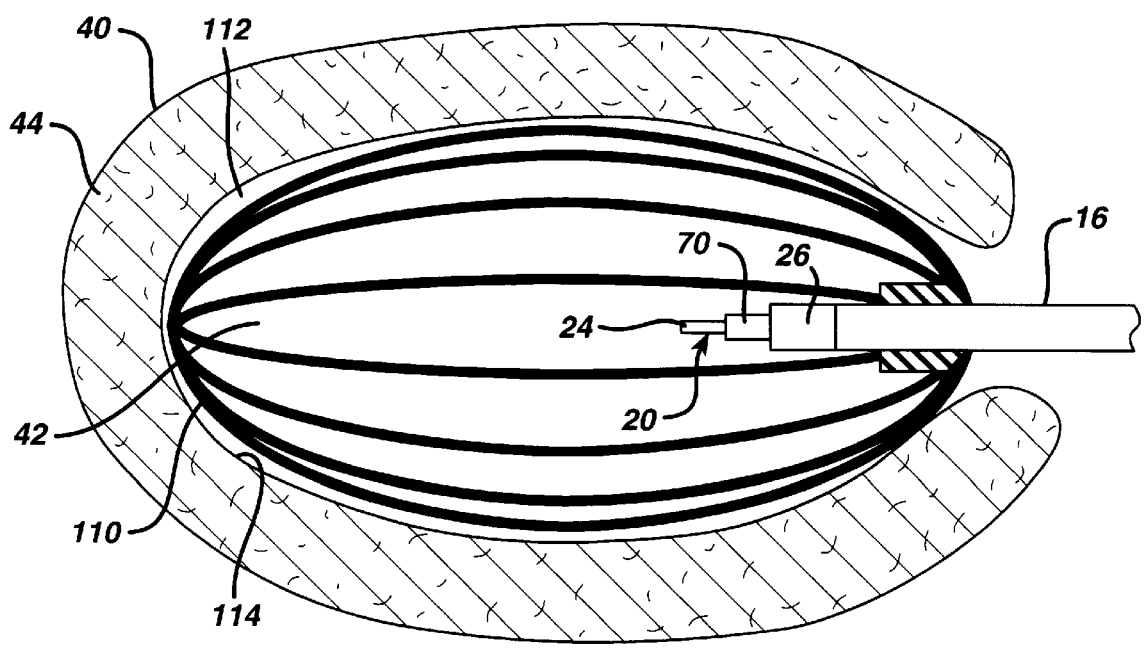
FIG. 9b is a side view of the device of FIG. 9a, showing the expandable cage in its deployed, expanded configuration.

In a further embodiment of the invention shown in FIGS. 9a and 9b, the bladder is replaced with an expandable cage 110. The cage 110 may be of a variety of materials and configurations, such as a simple steel "molly bolt" or similar design. The cage 110 surrounds the electrode assembly 20, which in the embodiment of FIG. 9a comprises an active electrode 24 and return electrode 26. In use, the expandable cage 110 is kept in its collapsed delivery configuration when the catheter shaft 16 is being introduced into a body cavity, such as a uterine cavity 112 as shown in FIG. 9a. Once inside the uterine cavity 112, the expandable cage 110 is expanded to its deployed configuration, as shown in FIG. 9b. The expandable cage 110 serves to hold the uterine cavity 112 open, and the expanded cavity is at least partially filled with conductive fluid 42. Because the conductive fluid 42 does not serve to hold the uterine cavity 112 open, the fluid pressure is low enough that not much fluid is forced through the uterine wall 114 to be absorbed by the patient.

When the electrode assembly 20 is activated, the conductive fluid 42 increases in temperature, and the uterine tissue walls 114 are ablated. If the conductive fluid 42 were at high pressure, such as might be necessary to expand the uterine cavity 112 with the fluid alone, the heated conductive fluid 42 might be readily forced through the uterine wall 114, which could cause unwanted thermal damage. However, since the expandable cage 110 serves to hold the uterine cavity 112 open, the conductive fluid 42 can be at relatively low pressure so that only relatively small amounts of conductive fluid 42 are forced into the uterine tissue wall 114.

The electrode assembly 20 in FIGS. 9a and 9b is a bipolar electrode having an active electrode 24 and a return electrode 26. The electrode assembly 20 may be of the type shown and described in pending U.S. application Ser. No. 08/702,512 entitled "An Electrosurgical Instrument," which is incorporated herein by reference. Such an electrode assembly could be used not only to heat the conductive fluid 42 but also to perform targeted procedures within the uterus or other body cavity, such as removal of fibroids and tumors. The operational characteristics of the electrode assembly are set forth in greater detail in the referenced pending application.

Figure 9C:
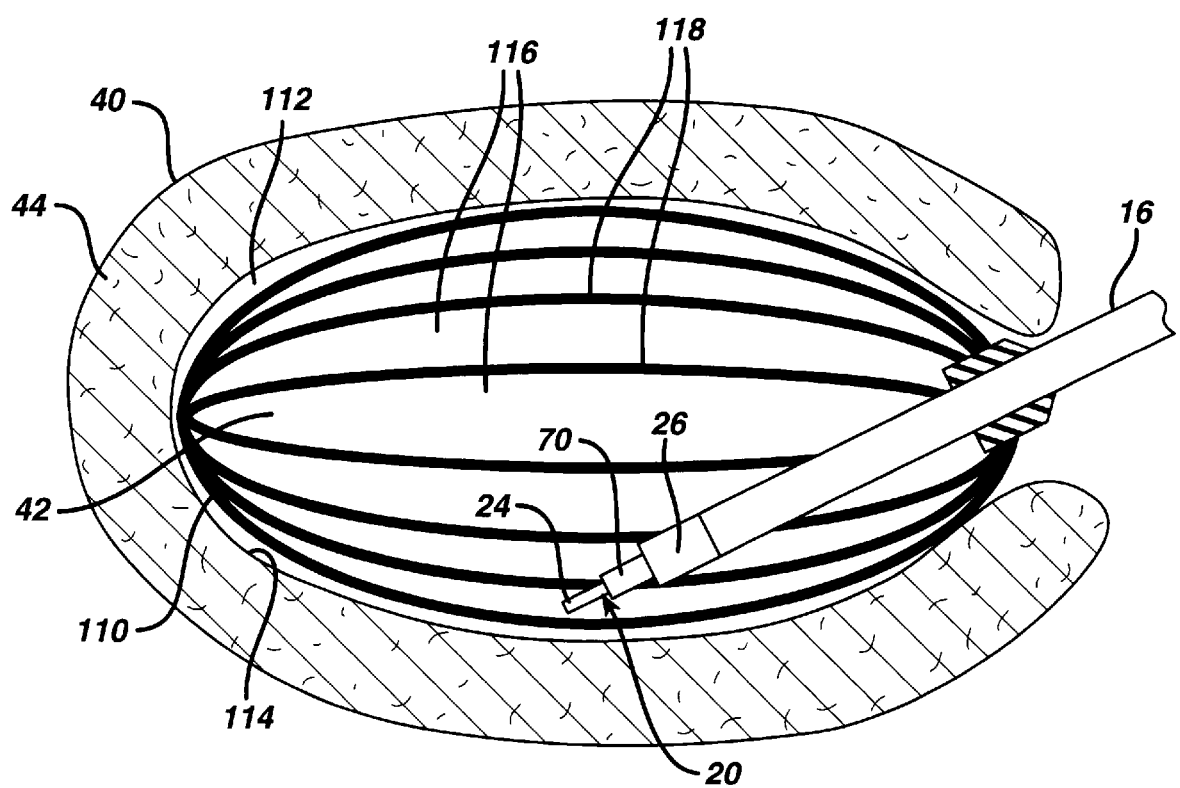
FIG. 9c is a side view of the device of FIGS. 9a and 9b, with the electrode assembly and catheter moved within the expandable cage.

The catheter shaft 16 may have a certain range of movement within the expandable cage 110, as shown in FIG. 9c, or even be able to be removed from and reintroduced into the cage 110. The expandable cage 110 may have large openings 116 between cage bars 118 to allow a user to access the uterine tissue surface 114 with the electrode assembly 20, such as may be required to selectively treat particular areas of the uterine surface. Thus, the expandable cage 110 of FIG. 9c allows the user to expand the uterine cavity 112 with the expandable cage 110, perform targeted procedures on the uterine wall 114 (such as removal of fibroids and tumors) with a bipolar electrode assembly 20, and then use that same electrode assembly 20 to heat the conductive fluid 42 to ablate the endometrial tissue 44.

The use of a catheter that is movable within an expandable member is particularly useful in combination with an endoscope or similar device for viewing within the body cavity. For example, a user may use a viewing device to determine if all areas of the tissue wall are properly ablated. Upon detecting areas that are not fully ablated, the user may move the catheter to position the electrode assembly at or near the non-ablated tissue, to thereby maximize the heating of the non-ablated tissue.

The movable catheter shaft can be used to selectively target tissue when used with the expandable cage of FIGS. 9a–9c, which allows the tissue to be viewed during the procedure. However, the movable catheter shaft may also be used with a distensible bladder, especially a distensible bladder that is substantially transparent so that a user can view the underlying tissue through the bladder wall. When the user determines that certain tissue areas are not ablated, the user can maneuver the electrode assembly to be adjacent the section of bladder wall immediately overlying the non-ablated tissue, thus increasing the heat delivered to the non-ablated tissue.

Referring again to FIG. 9c, where a particular portion of uterine wall tissue for targeted treatment is obstructed by a cage bar 118, the user could reposition the entire cage 110 in order to access the tissue portion. Alternatively, the expandable cage 110 might be designed to permit cage bars 118 to be individually moved without requiring relocation of the entire cage 110. Thus, a particular obstructing cage bar 118 could be moved to access a desired tissue portion.

Figure 10:
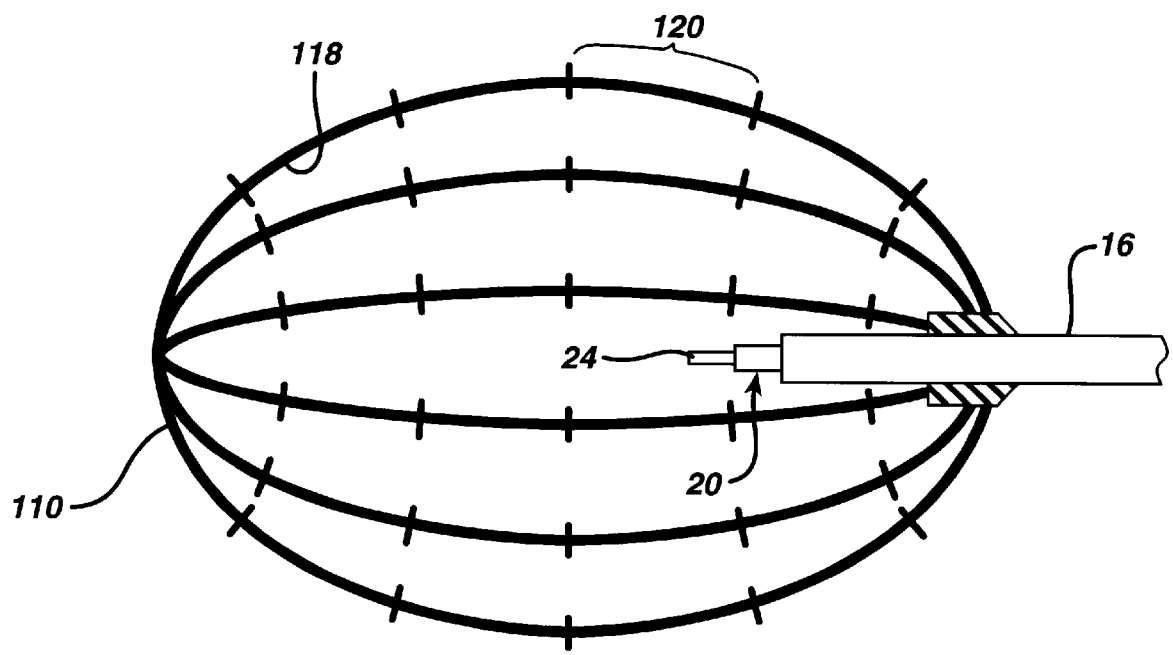
FIG. 10 is a side view, in partial section, of a further embodiment of the invention.

In the embodiment of FIG. 10, the active electrode 24 is located on the distal tip of the catheter shaft 16, but the expandable cage 110 itself serves as the return electrode. Such an embodiment performs similarly to the bladder with the conductive inner surface that was shown in FIG. 7. As portions of tissue are ablated, the adjacent portions of cage, which act as conductive return electrodes, increase in temperature, thereby increasing in impedance/resistivity. Accordingly, less energy is delivered to portions of cage adjacent to ablated tissue, and greater energy is delivered to portions of cage adjacent to non-ablated tissue.

As with the embodiment of FIG. 8, the expandable cage of FIG. 10 could have individual electrodes that were individually controlled, so that individual electrodes could be selectively shut off based on temperature, user selection, or other factors. For example, individual cage bars 118 could each be an individually-controlled electrode. Similarly, individual segments 120 of cage bars 118 could each be an individually-controlled electrode.

Figure 11:
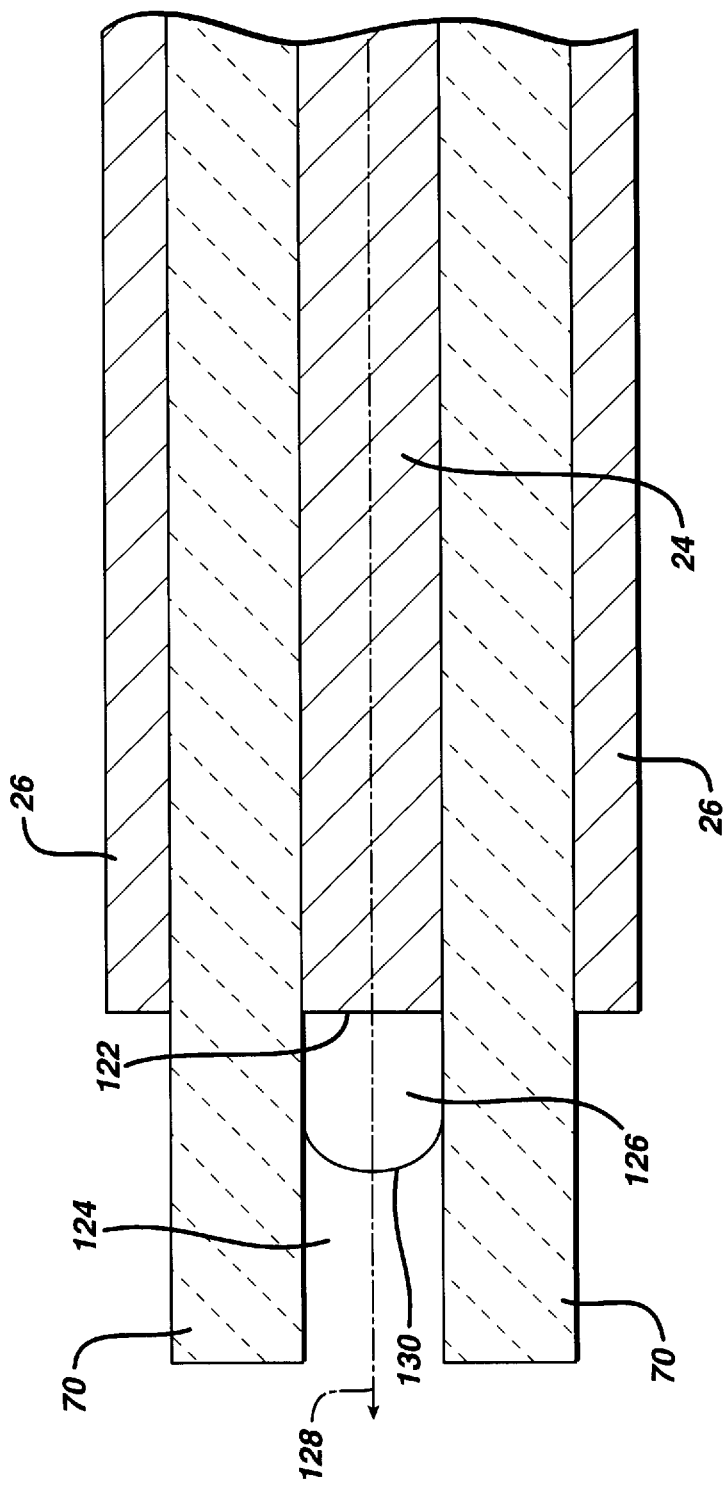
FIG. 11 is a side view, in section, of a pumping electrode according to an embodiment of the invention.

FIG. 11 shows an embodiment of a pumping electrode design having an electrode assembly 20 including of an active electrode 24 and a return electrode 26 separated by an insulator 70. The particular example shown has the return electrode 26 coaxial with and partially surrounding the active electrode 24. The active electrode 24 is encased in an insulator 70, with only the tip 122 of the active electrode 24 exposed. The insulator 70 creates a partial enclosure 124 about the exposed tip 122 of the active electrode 24.

When sufficient power is applied to the electrode assembly 20, a vapor pocket 126 forms in the partial enclosure 124 over the exposed tip 122 of the active electrode 24. By controlling the power delivered to the electrode assembly, the vapor pocket 126 can be made to pulse or oscillate. The oscillations of the vapor pocket 126, which necessarily cause the vapor pocket 126 to expand and contract in the direction of the longitudinal axis 128 of the electrode assembly 20, can be extremely vigorous. Under certain operating conditions, the vapor pocket 126 forms over the active electrode tip 122, then expands longitudinally to fill the partial enclosure 124. As the front 130 of the vapor pocket expands out of the partial enclosure 124, conductive fluid rushes in behind the vapor front 130, thereby partially collapsing the vapor pocket 126. The cycle is then repeated, with the vapor pocket 126 alternately expanding and collapsing.

Thus, the oscillations of the vapor pocket 126, combined with the partial enclosure 124, create a physical pumping action, thereby inducing flow away from the active electrode in the direction of the longitudinal axis 128. The pumping electrode embodiment may be particularly useful in combination with the moveable catheter shown in FIG. 9c. A user could thus maneuver pumping electrode assembly adjacent to selected tissue, and concentrate a flow of hot fluid to that selected tissue.

Figure 12:
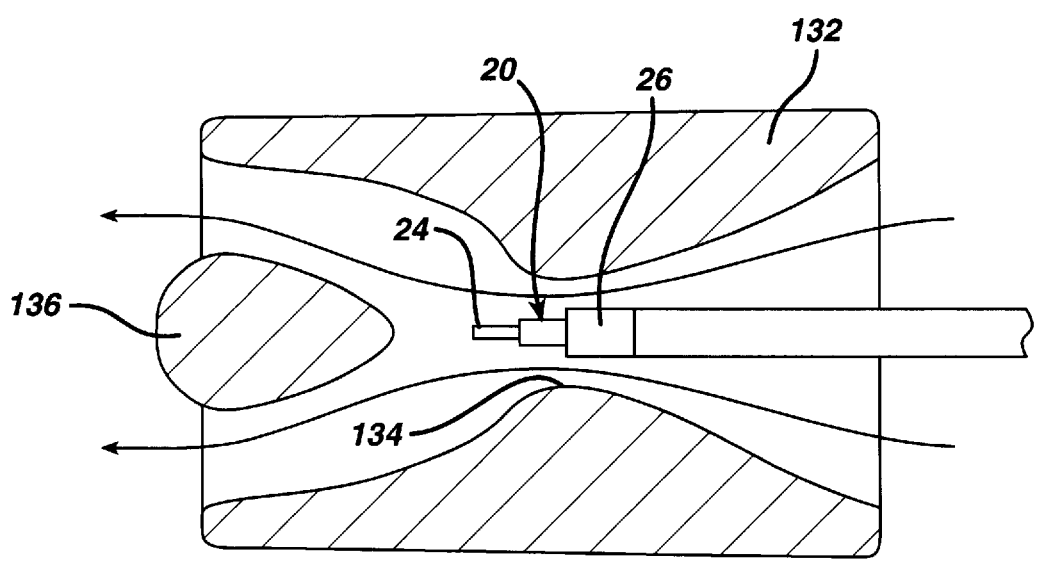
FIG. 12 is a side view, in partial section, of an electrode and nozzle according to an embodiment of the invention.

FIG. 12 shows another embodiment of an electrode assembly 20, including a nozzle 132 that enhances the pumping action of the electrode assembly 20. The nozzle 132 is shown in use with an electrode assembly 20 that employs the heat of the electrode assembly 20 to direct fluid flow. However, the nozzle 132 may also be used with a pumping electrode such as was shown in FIG. 11, or with an electrode that moves fluid using a magnetohydrodynamic effect.

The nozzle 132 may employ various jet-related propulsion techniques, such as ramjet theory. The nozzle 132 may be a venturi nozzle or similar device, serving to concentrate and direct the flow of fluid induced by the electrode assembly 20. In the embodiment shown in FIG. 12, the nozzle 132 is a venturi nozzle having a narrow throat 134, and the electrode assembly 20 is placed within the throat 134 of the nozzle. A diffuser 136 may be positioned downstream of the throat 134. When power is applied in a selected fashion to the electrode assembly 20, the fluid in the neck heats, inducing fluid flow generally along the longitudinal axis of the electrode assembly 20 in a direction toward the diffuser 136.

The nozzle may be particularly useful in combination with the moveable catheter shown in FIG. 9c. A user could thus maneuver the nozzle and electrode assembly adjacent to selected tissue, and concentrate a flow of hot fluid to that selected tissue.

Note that the invention shown and described herein would also operate if the polarities were reversed, so that the active electrodes became return electrodes, and the (formerly) return electrodes became active electrodes.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. An apparatus for treating tissue at a selected operation site, the apparatus comprising:
   a bladder; and
   a bipolar electrode assembly positioned within the bladder, said bipolar electrode assembly including an active electrode and a shield configured to prevent the active electrode from contacting the bladder.

2. The apparatus of claim 1, wherein the shield comprises a return electrode.

3. The apparatus of claim 2, wherein the return electrode is disposed on an inner surface of the shield, and the shield has an outer surface which is electrically non-conductive.

4. The apparatus of claim 1, wherein the shield further comprises one or more openings therethrough which allow a fluid to pass therethrough.

5. The apparatus of claim 1, wherein the bladder is filled with a conductive fluid.

6. The apparatus of claim 5, wherein the electrode assembly further comprises a return electrode, and the apparatus further comprises an RF power generator having bipolar outputs in electrical contact with the electrode assembly.

7. An apparatus for treating tissue at a selected operation site, the apparatus comprising:
   a bladder; and
   a bipolar electrode assembly positioned within the bladder, said bipolar electrode assembly including an active electrode and a return electrode, wherein the active electrode has an effective area, and the return electrode has an effective area different from the active electrode effective areas,
   wherein the return electrode effective area is at least twice as large as the active electrode effective area,
   wherein the active electrode is at a distal tip of the shaft, the return electrode is proximal to the return electrode on the shaft, and further comprising an insulator between the active electrode and return electrode, and
   wherein the return electrode is coaxial with the active electrode.

8. The apparatus of claim 7, further comprising an RF power generator having bipolar outputs in electrical contact with the electrode assembly.

9. An apparatus for delivering controlled heat to a selected operation site, the apparatus comprising:
   an expandable device, wherein the expandable device has a delivery configuration and an expanded configuration, wherein the expandable device may be transformed from the delivery configuration to the expanded configuration and subsequently returned to the delivery configuration;
   a shaft having a distal end disposed within the expandable device, said shaft configured for movement within the expandable device, wherein the shaft passes through an opening in the expandable device, and said shaft is configured for pivotal movement within said opening; and
   an electrode assembly at the shaft distal end.

10. The apparatus of claim 9, wherein said shaft is configured to longitudinally move within said opening.

11. The apparatus of claim 9, wherein the expandable device is an expandable cage.

12. The apparatus of claim 9, wherein the expandable device is a distensible bladder.

13. An apparatus for delivering controlled heat to a selected operation site, the apparatus comprising:
   a shaft having a distal end;
   an electrode assembly at the shaft distal end, said electrode assembly comprising at least one active electrode and at least one return electrode; and
   a mechanically expandable device for the shaft distal end, wherein the mechanically expandable device has a delivery configuration and an expanded configuration, wherein the mechanically expandable device may be transformed from the delivery configuration to the expanded configuration and subsequently returned to the delivery configuration, the mechanical device in the expanded configuration defining a space therein, wherein at least one of said electrodes is positioned within said defined space,
   wherein the mechanically expandable device comprises an expandable cage, and
   wherein at least one of said electrodes is disposed on the mechanically expandable device.

14. An apparatus for delivering controlled heat to a selected operation site, the apparatus comprising:
   a shaft having a distal end;
   a mechanically expandable device at the shaft distal end, wherein the mechanically expandable device has a delivery configuration and an expanded configuration; and
   an electrode assembly at the shaft distal end, said electrode assembly comprising at least one active electrode and a plurality of return electrodes, wherein said return electrodes are disposed on the mechanically expandable device.

15. A method of treating tissue using a surgical device, wherein the surgical device has a distal end having an expandable device and a bipolar electrode assembly thereon, the bipolar electrode assembly comprising at least one active electrode and at least one return electrode, the method comprising the steps of:

(a) introducing the distal end of the surgical device into a selected operation site;

(b) expanding the expandable device, wherein the expandable device comprises an expandable cage having a plurality of cage bars, said cage bars having underlying portions of the tissue when the expandable cage is in the expanded configuration;

(c) filling the expandable device with a conductive fluid;

(d) applying RF output power to the bipolar electrode assembly to cause current to flow between the active electrode and the return electrode through the conductive fluid, thereby increasing the temperature of the conductive fluid;

(e) monitoring the impedance between the active electrode and return electrode;

(f) determining the temperature of the conductive fluid from the monitored impedance;

(g) positioning the bipolar electrode assembly at a location within the expandable device which is adjacent specifically targeted tissue;

(h) applying RF output power to the bipolar electrode assembly to effect treatment of the specifically targeted tissue;

(i) moving one or more cage bars to reveal the underlying tissue;

(j) placing the bipolar electrode assembly adjacent to the revealed underlying tissue; and (k) applying output power to the bipolar electrode assembly sufficient to effect treatment of the revealed underlying tissue.

16. The method of claim 15, wherein step (c) comprises the step of filling the expandable device with a saline solution.

* * * * *